United States Patent

Hayashi et al.

[11] Patent Number: 6,060,496
[45] Date of Patent: May 9, 2000

[54] PROPHYLAXIS AND TREATMENT OF DIABETIC COMPLICATIONS WITH 4-[α-HYDROXY-2-METHYL-5-(1-IMIDAZOLYL)BENZYL]-3,5-DIMETHYLBENZOIC ACID

[75] Inventors: Yoshiharu Hayashi; Nobuharu Goto, both of Iruma, Japan

[73] Assignee: Yoshitomi Pharmaceutical Industires, Ltd., Japan

[21] Appl. No.: 09/091,993

[22] PCT Filed: Dec. 24, 1996

[86] PCT No.: PCT/JP96/03776

§ 371 Date: Jun. 26, 1998

§ 102(e) Date: Jun. 26, 1998

[87] PCT Pub. No.: WO97/24333

PCT Pub. Date: Jul. 10, 1997

[30] Foreign Application Priority Data

Dec. 27, 1995 [JP] Japan ................................ 7-340161

[51] Int. Cl.[7] .................... A61K 31/415; C07D 233/60; C07D 233/101
[52] U.S. Cl. .................... 514/400; 514/399; 548/341.5
[58] Field of Search ................ 548/341.5; 514/400, 514/399

[56] References Cited

U.S. PATENT DOCUMENTS

| | | | |
|---|---|---|---|
| 4,448,781 | 5/1984 | Cross et al. | 424/269 |
| 4,661,603 | 4/1987 | Tsuruda et al. | 548/341.5 X |
| 4,737,506 | 4/1988 | Shimizu et al. | 514/332 |
| 4,882,347 | 11/1989 | Cozzi et al. | 514/396 |
| 5,091,191 | 2/1992 | Oda et al. | 514/399 |

FOREIGN PATENT DOCUMENTS

| | | | |
|---|---|---|---|
| 0 379 579 | 8/1990 | European Pat. Off. | |
| 38 18 741 | 12/1988 | Germany | 514/396 |
| 61-277670 | 12/1986 | Japan | |
| 63-119425 | 5/1988 | Japan | |
| 2-704 | 1/1990 | Japan | |
| 3-7281 | 1/1991 | Japan | |
| 0 427 860 | 5/1991 | Japan | |

OTHER PUBLICATIONS

M. Tsuruda et al., *J. Pharm. Soc. Jap.*, 109(1), 26–32 (1989).
W. Erdbrügger et al., *Prog. Clin. Biol. Res.*, 301, 389–394 (1989).
Y. Ono et al., *Prostaglandins Leukot. Essent. Fatty Acids*, 53, 139–145 (Aug. 1995).
H. Sone et al., *Life Sciences*, 58(3), 239–243 (1996).
C. Patrono et al., *J. Lipid Mediators*, 6, 411–415 (1993).
Y. Matsuo et al., *Pharmacology*, 50(1), 1–8 (Jan. 1995).
K. Hora et al., *Nephron*, 56(3), 297–305 (1990).
S. Katayama et al., *J. Lab. Clin. Med.*, 109(6), 711–717 (1987).

*Primary Examiner*—Floyd D. Higel
*Attorney, Agent, or Firm*—Wenderoth, Lind & Ponack, L.L.P.

[57] ABSTRACT

The present invention relates to an agent for the prophylaxis and treatment of diabetic complications comprising, as an active ingredient, 4-[α-hydroxy-2-methyl-5-(1-imidazolyl)benzyl]-3,5-dimethylbenzoic acid, an optically active compound thereof or a pharmaceutically acceptable salt thereof. The present invention further relates to a method for the prophylaxis and treatment of diabetic complications comprising administering an effective amount of this compound. The medicament of the present invention is useful for the prophylaxis and treatment of diabetic complications, namely, diabetic neuropathy, nephropathy, ophthalmopathy, arteriosclerosis and the like. The action of the drug is long-lasting for very small doses and a single administration a day is sufficient.

4 Claims, No Drawings

PROPHYLAXIS AND TREATMENT OF DIABETIC COMPLICATIONS WITH 4-[α-HYDROXY-2-METHYL-5-(1-IMIDAZOLYL)BENZYL]-3,5-DIMETHYLBENZOIC ACID

Technical Field

The present invention relates to an agent for the prophylaxis and treatment of diabetic complications, namely, to an agent for the prophylaxis and treatment of diabetic neuropathy, nephropathy, ophthalmopathy and arteriosclerosis. More particularly, the present invention relates to an agent for the prophylaxis and treatment of diabetic complications comprising, as an active ingredient, 4-[α-hydroxy-2-methyl-5-(1-imidazolyl)benzyl]-3,5-dimethylbenzoic acid, an optically active compound thereof or a pharmaceutically acceptable salt thereof. The present invention further relates to a method for the prophylaxis and treatment of diabetic complications.

BACKGROUND ART

The discovery of insulin and its clinical application resulted in drastic progress in the treatment of diabetes. Life sustention of the patients with diabetes—which had been a deadly disease until then—was strikingly improved. However, the therapy of chronic complications of diabetes has become a new problem.

The therapy of diabetes aims at prevention of such chronic complications, and essentially consists of a further control of blood glucose and a direct therapy of complications. The major chronic complications of diabetes are known to be neuropathy, nephropathy, ophthalmopathy, arteriosclerosis and the like (David M. et al., N. Engl. J. Med., 328, p. 1676–1685(1993)).

Various factors have been considered to be responsible for the onset and progression of chronic complications of diabetes. For example, there are known an abnormal sorbitol metabolism theory wherein activity promotion of sorbitol-producing polyol metabolitic pathway is the cause (Gabbay K. H. et al., N. Engl. J. Med. 288, p. 831–837(1973)), a circulatory disorder theory wherein a causative factor is a decreased blood flow due to angiopathy (Dyck P. J. et al, Proc. Natl. Acad. Sci. USA, 82, p. 2513–2517 (1985)), a theory attributing the disease to a compound produced by non enzymatic binding reaction of protein and reducing glucose (AGE: advanced glycation endproduct) (Brownlee M. et al., N. Engl. J. Med. 318, p. 1315–1321 (1988)) and the like. Based on each hypothesis, an aldose reductase inhibitor and lipoprostaglandin E1have been developed, and an AGE production inhibitor is under development.

The diabetic patients show promoted platelet aggregation, and the mechanism thereof has been known to be the promotion of biosynthesis of thromboxane (hereinafter abbreviated as TX) A2 due to hyperglycemia. This is considered to be one of the pathogens of diabetic chronic complications (Giovanni Davi M. D. et al., N. Engl. J. Med. 322, p. 1769–1774 (1990)). Thus, lipoprostaglandin E1 (hereafter sometimes to be referred to as Lipo PGE 1) having peripheral circulation improving action or platelet aggregation inhibitory action, 6-[4-(1 -cyclohexyl-1,2,3,4-tetrazol-5-yl)butoxy]-3,4-dihydrocarbostyryl(cilostazol) and 6-[4-(R)-chlorophenylsulfonamido]-1-(3pyridylmethyl)pyrrolidin-2(S)-yl)-5-(Z)-hexenoic acid.hydrochloride (investigational numer: KDI-792) having TXA2 receptor antagonistic/synthesis inhibitory activity have been under development as agents for the prophylaxis and treatment of diabetic complications.

On the other hand, Japanese Patent Examined Publication No. 41143/1993 discloses 4-[α-hydroxy-2-methyl-5-(1-imidazolyl)benzyl]-3,5-dimethylbenzoic acid having pharmacological activities such as strong TXA2 biosynthesis inhibitory activity, platelet aggregation inhibitory action, vasodilating action and the like, which is useful for the prophylaxis and treatment of thrombosis, cerebral hemorrhage, myocardial infarction, acute cardiac death, angina pectoris, hypertension, asthma, nephritis and the like, an optically active compound and a pharmaceutically acceptable salt thereof. Nevertheless, it is not known that these compounds act as agents for the prophylaxis and treatment of diabetic complications.

Under the circumstances, the development of a new therapeutic agent that acts directly on chronic complications of diabetes for the prophylaxis and treatment of diabetes, which is capable of providing a better quality of life has been desired.

The Lipo PGE 1, cilostazol, KDI-792 and the like, which are under development as agents for the prophylaxis and treatment of diabetic complications based on the above-mentioned peripheral circulation improving activity, platelet aggregation inhibitory activity and TXA2 receptor antagonistic/synthesis inhibitory activity, all exhibit only a short duration of activity and require 2 to 3 times of administration a day. Considering the quality of life of the patients with diabetes, they are remotely sufficient The present inventors have confirmed that sodium ozagrel [sodium(E)-p-(imidazol-1-ylmethyl)cinnamate] having TXA2 synthesis inhibitory activity suppresses promotion of biosynthesis of TXA2 in rats with diabetes, but does not improve decreased tail nerve conduction velocity. This suggests that not every TXA2 synthesis inhibitor is effective for diabetic complications.

DISCLOSURE OF THE INVENTION

The present inventors have conducted intensive studies from this viewpoint and found that 4-[α-hydroxy-2-methyl-5-(1-imidazolyl)benzyl]-3,5-dimethylbenzoic acid, an optically active compound thereof and a pharmaceutically acceptable salt thereof, having pharmacological activities of TXA2 biosynthesis inhibitory activity, platelet aggregation inhibitory activity and vasodilating action, are useful for the prophylaxis and treatment of diabetic complications, namely, for the prophylaxis and treatment of diabetic neuropathy, nephropathy, ophthalmopathy and arteriosclerosis, and that the activity thereof is long-lasting for small doses, thus enabling a single administration a day, which resulted in the completion of the present invention.

Accordingly, the present invention provides the following.

1) An agent for the prophylaxis and treatment of diabetic complications, comprising 4-[α-hydroxy-2-methyl-5-(1-imidazolyl)benzyl]-3,5-dimethylbenzoic acid, an optically active compound or a pharmaceutically acceptable salt thereof as an active ingredient.
2) An agent for the prophylaxis and treatment of diabetic complications, comprising sodium 4-[α-hydroxy-2-methyl-5-(1-imidazolyl)benzyl]-3,5-dimethylbenzoate dihydrate as an active ingredient.
3) An agent for the prophylaxis and treatment of diabetic complications, comprising (S)-(-)-4[α-hydroxy-2-methyl-5-(1-imidazolyl)benzyl]-3,5,-dimethylbenzoic acid or a pharmaceutically acceptable salt thereof as an active ingredient.
4) An agent for the prophylaxis and treatment of diabetic complications, comprising sodium (S)-(-)-4-[α-hydroxy- 2-methyl-5-(1imidazolyl)benzyl]-3,5 -dimethylbenzoate 2/3 hydrate as an active ingredient.

5) The agent for the prophylaxis and treatment of the above 1) to 4), wherein the diabetic complication is at least one member selected from the group consisting of neuropathy, nephropathy, ophthalmopathy and arteriosclerosis.

6) The agent for the prophylaxis and treatment of the above 1) to 4), wherein the diabetic complication is neuropathy.

7) The agent for the prophylaxis and treatment of the above 1) to 4), wherein the diabetic complication is nephropathy.

8) The agent for the prophylaxis and treatment of the above 1) to 4), wherein the diabetic complication is ophthalmopathy.

9) The agent for the prophylaxis and treatment of the above 1) to 4), wherein the diabetic complication is arteriosclerosis.

10) A method for the prophylaxis and treatment of diabetic complications, comprising administering an effective amount of 4-[α-hydroxy-2-methyl-5-(1-imidazolyl) benzyl]-3,5-dimethylbenzoic acid, an optically active compound thereof or a pharmaceutically acceptable salt thereof.

11) A method for the prophylaxis and treatment of diabetic complications, comprising administering an effective amount of sodium 4-[α-hydroxy-2-methyl-5-(1imidazolyl)benzyl]-3,5-dimethylbenzoate dihydrate.

12) A method for the prophylaxis and treatment of diabetic complications, comprising administering an effective amount of (S)-(-)-4-[α-hydroxy-2-methyl-5-(1-imidazolyl)benzyl]-3,5-dimethylbenzoic acid or a pharmaceutically acceptable salt thereof.

13) A method for the prophylaxis and treatment of diabetic complications, comprising administering an effective amount of sodium (S)-(-)-4-[α-hydroxy-2-methyl-5-(1-imidazolyl)benzyl ]3,5-dimethylbenzoate 2/3 hydrate.

14) The method of any one of the above 10) to 13) wherein the diabetic complication is at least one member selected from the group consisting of neuropathy, nephropathy, ophthalmopathy and arteriosclerosis.

15) The method of any one of the above 10) to 13) wherein the diabetic complication is neuropathy.

16) The method of any one of the above 10) to 13) wherein the diabetic complication is nephropathy.

17) The method of any one of the above 10) to 13) wherein the diabetic complication is ophthalmopathy.

18) The method of any one of the above 10) to 13) wherein the diabetic complication is arteriosclerosis.

19) Use of 4-[α-hydroxy-2-methyl-5-(1-imidazolyl)benzyl]-3,5-dimethylbenzoic acid, an optically active compound thereof or a pharmaceutically acceptable salt thereof for the production of a medicament for the prophylaxis and treatment of diabetic complications.

20) Use of sodium 4-[α-hydroxy-2-methyl-5-(1-imidazolyl) benzyl]-3,5-dimethylbenzoate dihydrate for the production of a medicament for the prophylaxis and treatment of diabetic complications.

21) Use of (S)-(-)-4-[α-hydroxy-2-methyl-5-(1-imidazolyl) benzyl]-3,5dimethylbenzoic acid or a pharmaceutically acceptable salt thereof for the production of a medicament for the prophylaxis and treatment of diabetic complications.

22) Use of sodium (S)-(-)-4-[α-hydroxy-2-methyl-5-(1-imidazolyl)benzyl]-3,5-dimethylbenzoate 2/3 hydrate for the production of a medicament for the prophylaxis and treatment of diabetic complications.

23) The use of any one of the above 19) to 22) wherein the diabetic complication is at least one member selected from the group consisting of neuropathy, nephropathy, ophthalmopathy and arteriosclerosis.

24) The use of any one of the above 19) to 22) wherein the diabetic complication is neuropathy.

25) The use of any one of the above 19) to 22) wherein the diabetic complication is nephropathy.

26) The use of any one of the above 19) to 22) wherein the diabetic complication is ophthalmopathy.

27) The use of any one of the above 19) to 22) wherein the diabetic complication is arteriosclerosis.

28) A pharmaceutical composition for the prophylaxis and treatment of diabetic complications, which comprises an effective amount of 4-[α-hydroxy-2-methyl-5-(1-imidazolyl)benzyl]-3,5-dimethylbenzoic acid, an optically active compound thereof or a pharmaceutically acceptable salt thereof, and a pharmaceutically acceptable carrier.

29) A pharmaceutical composition for the prophylaxis and treatment of diabetic complications, which comprises an effective amount of sodium 4-[α-hydroxy-2-methyl-5-(1-imidazolyl)benzyl]-3,5-dimethylbenzoate dihydrate and a pharmaceutically acceptable carrier.

30) A pharmaceutical composition for the prophylaxis and treatment of diabetic complications, which comprises an effective amount of (S)-(-)-4-[α-hydroxy-2-methyl-5-(1-imidazolyl)benzyl]-3,5-dimethylbenzoic acid or a pharmaceutically acceptable salt thereof, and a pharmaceutical acceptable carrier.

31) A pharmaceutical composition for the prophylaxis and treatment of diabetic complications, which comprises an effective amount of sodium (S)-(-)-4-[α-hydroxy-2-methyl-5-(1-imidazolyl)benzyl]-3,5dimethylbenzoate 2/3 hydrate and a pharmaceutically acceptable carrier.

32) The pharmaceutical composition of any one of the above 28) to 31) wherein the diabetic complication is at least one member selected from the group consisting of neuropathy, nephropathy, ophthalmopathy and arteriosclerosis.

33) The pharmaceutical composition of any one of the above 28) to 31) wherein the diabetic complication is neuropathy.

34) The pharmaceutical composition of any one of the above 28) to 31) wherein the diabetic complication is nephropathy.

35) The pharmaceutical composition of any one of the above 28) to 31) wherein the diabetic complication is ophthalmopathy.

36) The pharmaceutical composition of any one of the above 28) to 31) wherein the diabetic complication is arteriosclerosis.

37) A commercial package comprising the pharmaceutical composition of any one of the above 28) to 31) and a written matter associated therewith, the written matter stating that said pharmaceutical composition can or should be used for the prophylaxis and treatment of diabetic complications.

DETAILED DESCRIPTION OF THE INVENTION

The action as the agent for the prophylaxis and treatment of diabetic complications of the present invention, namely, the action as the agent for the prophylaxis and treatment of neuropathy, nephropathy, ophthalmopathy and arteriosclerosis, can be confirmed through rat tail nerve conduction velocity, sciatic nerve conduction velocity, degree of glomerular disorder, amount of urinary albumin excretion, degree of cataract examining funduscopy, degree of hypertrophy and the like.

Of the diabetic complications in the present invention, neuropathy means symmetric polyneuropathy of sensory, motor and autonomic nerves, and local or polydomous neuropathy of cerebral nerve; and ophthalmopathy means cataract, glaucoma, retinopathy, iritis and the like.

The compounds of the present invention can be synthesized by the methods descibed in Japanese Patent Examined Publication No. 41143/1993 and Japanese Patent Unexamined Publication No. 215771/1990.

The pharmaceutically acceptable salts of the compounds of the present invention include, for example, salts with inorganic acid such as hydrochloric acid, hydrobromic acid and sulfuric acid; acid addition salts with organic acid such as fumaric acid, maleic acid, mandelic acid, citric acid, tartaric acid, salicylic acid and the like; salts with metal such as sodium, potassium, lithium, calcium, magnesium, zinc and aluminum and salts with amino acid such as lysine. Further, hydrates, such as 1/2 hydrate, 1/3 hydrate, 2/3 hydrate, monohydrate, 3/2 hydrate and dihydrate, are also encompassed.

Preferable compounds of the present invention include sodium 4-[α-hydroxy-2-methyl-5-(1-imidazolyl)benzyl]-3,5-dimethylbenzoate dihydrate (hereinafter sometimes referred to as compound A-1), sodium (S)-(-)-4-[α-hydroxy-2-methyl-5-(1-imidazolyl)benzyl]-3,5-dimethylbenzoate 2/3 hydrate (hereinafter sometimes referred to as compound A-2), sodium (R)-(+)-4-[α-hydroxy-2-methyl-5-(1-imidazolyl)benzyl]-3,5-dimethylbenzoate 2/3 hydrate (hereinafter sometimes referred to as compound A-3), (S)-(-)-4-[α-hydroxy-2-methyl-5-(1-imidazolyl)benzyl]-3,5-dimethylbenzoic acid hereinafter sometimes referred to as compound A4), and (R)-(+)-4-[α-hydroxy-2-methyl-5-(1-imidazolyl)benzyl]-3,5-dimethylbenzoic acid (hereinafter sometimes referred to as compound A-5). Compound A-1 is crystals having a melting point of 271–285° C. Compound A-2 has an optical rotation of $[\alpha]_D^{23.5}$ −149.5° (c=1.0, water), an optical rotation of compound A-3 is $[\alpha]_D^{24}$+ 147.2° (c=1.0, water) and compound A4 has a melting point of 286–288° C. (decomposition) and an optical rotation of $[\alpha]_D^{21}$ −261.5° (c=1.0, dimethylformamide), and compound A-5 has a melting point of 286–287° C. (decomposition) and an optical rotation of $[\alpha]_D^{21}$+260.5° (c=1.0, dimethylformamide).

The agent for the prophylaxis and treatment of diabetic complications according to the present invention is formulated as a general pharmaceutical preparation. For example, the compound of the present invention is formulated into a dosage form suitable for oral or parenteral administration, such as a pharmaceutical composition or tablet, pill, powder, granule, capsule, troche, syrup, liquid, emulsion, suspension, injection (liquid, suspension), suppository, inhalant, percutaneous absorber, eye drop, eye ointment and the like, which is produced by admixing the compound with a pharmaceutically acceptable carrier (e.g., excipient, binder, disintegrator, corrective, corrigent, emulsifier, diluent, solubilizer and the like). When a solid preparation is prepared, an additive is used, such as sucrose, lactose, cellulose, D-mannitol, maltitol, dextran, starch, agar, arginates, chitins, chitosans, pectin, tragcanth gums, gum arabic, gelatins, collagens, casein, albumin, calcium phosphate, sorbitol, Sine, carboxymethylcellulose, polyvinylpyrrolidone, hydroxypropylcellulose, hydroxypropylmethylcellulose, glycerol, polyethylene glycol, sodium hydrogencarbonate, magnesium stearate, talc and the like. Where necessary, tablets are prepared to have an ordinary tablet coating to give, for example, sugar-coated tablet, enteric-coated tablet, film-coated tablet or two-layer tablet or multi-layer tablet When a semi-solid preparation is to be produced, animal and plant fats and oils (e.g., olive oil, corn oil, castor oil and the like), mineral oil and fats (e.g., petrolatum, white petrolatum, solid paraffin and the like), wax (e.g., jojoba oil, carnauba wax, yellow bees wax and the like), partially synthesized or entirely synthesized glycerol fatty acid ester (e.g., lauric acid ester, myristic acid ester, palmitic acid ester and the like) and the hle are used. Examples of commercially available products thereof include Witepsol (manufactured by Dynamite Nobel), Pharmasol (manufactured by NOF Corporation) and the like.

When a liquid preparation is to be produced, an additive such as sodium chloride, sorbitol, glycerol, olive oil, propylene glycol, ethyl alcohol and the like is used. Particularly when an injection is to be produced, a sterile aqueous solution (e.g., physiological saline and isotonic solution) or oily liquid (e.g., sesame oil and soy bean oil) is used. Where necessary, an adequate suspending agent (e.g., sodium carboxymethylcellulose), non-ionic surfactant, solubilizer (e.g., benzyl benzoate and benzyl alcohol) and the like may be also used. When an eye drop is to be produced, an aqueous liquid or aqueous solution is used, which is particular a sterile aqueous solution for injection. This eye drop liquid may contain various additives as appropriate, such as buffer (preferably, borate buffer, acetate buffer, carbonate buffer and the like are used for reducing irritation), isotonizing agent, solubilizer, preservative, thickener, chelating agent, pH adjusting agent (preferably, pH is generally adjusted to about 6–8.5), aromatic and the like.

The amount of the active ingredient of these preparation is 0.1–100 wt %, suitably 1–50 wt %, of the preparation. The dose varies depending on the symptom, body weight, age and the like of patients. In the case of oral administration, the dose is gently about 0.01–50 mg/kg body weight/day for an adult, which is preferably administered in a single dose or several doses.

EXAMPLES

The agent for the prophylaxis and treatment of diabetic complications of the present invention is explained more specifically by way of Formulation Examples and pharmacological activity. It should be noted that the present invention is not limited to these exemplifications.

Formulation Example 1:Film-coated tablet

| | |
|---|---|
| Compound A-1 | 50.0 mg |
| D-mannitol | 70.5 mg |
| Corn starch | 16.0 mg |
| Sodium hydrogencarbonate | 15.0 mg |
| Hydroxypropylmethylcellulose | 3.0 mg |
| Talc | 5.0 mg |
| Magnesium stearate | 0.5 mg |

Compound A-1, D-mannitol, corn starch and sodium hydrogencarbonate were mixed and an aqueous solution of hydroxypropylmethylcellulose was sprayed for flow granulation. The granules were passed through a 24-mesh sieve, and talc and magnesium stearate were added. The mixture was processed in a rotary compressor (Kikusui Seisakusho) to give tablets each weighing 160 mg. Then, a film coating agent comprising hydroxypropylmethylcellulose as a film coating base was applied at 6 mg per tablet Formulation Example 2: Fine granules

| Compound A-1 | 10% |
|---|---|
| D-mannitol | 89.5% |
| Hydroxypropylcellulose | 0.5% |

Compound A-1 and D-mannitol were mixed and an aqueous solution of hydroxypropylcellulose was added. The mixture was kneaded, which was followed by granulation and drying at 50° C. The granules were passed through a 32-mesh sieve to give fine granules.

Formulation Example 3: Tablets

| Compound A-1 | 50.0 mg |
|---|---|
| D-mannitol | 30.0 mg |
| Corn starch | 19.0 mg |
| Sodium hydrogencarbonate | 15.0 mg |
| Hydroxypropylmethylcellulose | 1.5 mg |
| Talc | 4.0 mg |
| Magnesium stearate | 0.5 mg |

Compound A-1, D-mannitol, corn starch and sodium hydrogencarbonate were mixed and an aqueous solution of hydroxypropylmethylcellulose was sprayed for flow granulation. The granules were passed through a 24-mesh sieve, and talc and magnesium stearate were added. The mixture was processed in a rotary compressor (Kikusui Seisakusho) to give tablets each weighing 120 mg.

Formulation Example 4: Fine granules

| Compound A-2 | 5% |
|---|---|
| D-mannitol | 92% |
| Hydroxymethylpropylcellulose | 3% |

Compound A-2 and D-mannitol were mixed and an aqueous solution of hydroxypropylmethylcellulose was added. The mixture was kneaded, which was followed by granulation and drying at 50° C. The granules were passed through a 32-mesh sieve to give fine granules.

The pharmacological activity of the pharmaceutical agent of the present invention is explained by way of Experimental Examples.

Experimental Example 1

Diabetes was induced by intravenous administration of streptozotocin (65 mg/kg to 6-week-old male Sprague-Dawley rats. Starting from 2–4 weeks after the onset of diabetes, a 0.5% hydroxypropylmethylcellulose suspension containing the compound of the present invention was orally administered once a day. At 4–7 weeks from the administration, tail nerve conduction velocity was measured with an induction potential test device (Neuropack 2, manufactured by Nihon Kohden) according to a modification of the method of Miyoshi (Fukuoka Medical Journal, vol. 62, pp. 588–603 (1971)). To be specific, subcutaneous temperature at the tail was maintained at 37° C. and the tail nerve was percutaneously stimulated electrically at 2 stimulation points (interval 6 cm). The distance between stimulation points was divided by the difference between latencies in electromyogram induced to give nerve conduction velocity. As to the test group in Table 1, blood glucose was measured at 6 weeks after administration. At 7 weeks after administration, urinary excretion of TXB2, which is a stable metabolite of TXA2, was measured.

TABLE 1

| test group | dose mg/kg/day | blood glucose mg/dl | urinary TXB2 excretion ng/day/100 g body weight | tail nerve conduction velocity m/sec 7 wks after administration |
|---|---|---|---|---|
| Control group | 0 | 122.0 ± 3.8** | 4.1 ± 0.4** | 44.6 ± 0.5** |
| Diabetes group | 0 | 870.3 ± 78.5 | 16.9 ± 1.7 | 41.3 ± 0.5 |
| Compound A-1 Administered group | 0.03 | 718.3 ± 50.7 | 10.6 ± 1.4** | 42.0 ± 0.5 |
| Compound A-1 Administered group | 0.1 | 772.1 ± 32.4 | 6.9 ± 0.8** | 43.4 ± 0.4** |
| Compound A-1 Administered group | 0.3 | 791.9 ± 65.5 | 5.1 ± 0.5** | 43.7 ± 0.3** |
| Compound A-1 Administered group | 1.0 | 718.4 ± 64.1 | 3.4 ± 0.3** | 44.8 ± 0.4** |

The data was shown by mean±standard error of 11–12 rats per group. Each group was compared to diabetes group by Dunnett's test (**P<0.01).

From the above-mentioned results of Experimental Example, the compound A-1 of the present invention decreased urinary TXB2 excretion that had been increased by diabetes, and increased tail nerve conduction velocity which had been decreased by diabetes, in a dose-dependent manner without affecting the blood glucose.

TABLE 2

| test group | dose mg/kg/day | tail nerve conduction velocity m/sec 5 wks after administration |
|---|---|---|
| Control group | 0 | 43.7 ± 0.4** |
| Diabetes group | 0 | 39.4 ± 0.2 |
| Compound A-2 Administered group | 0.03 | 40.7 ± 0.5** |
| Compound A-2 Administered group | 0.1 | 42.6 ± 0.4** |
| Compound A-2 Administered group | 0.3 | 43.0 ± 0.3** |
| Compound A-2 Administered group | 1 | 42.6 ± 0.5** |

The data was shown by mean±standard error of 10 rats per group. Each group was compared to diabetes group by Dunnett's test (**P<0.01).

TABLE 3

| test group | dose mg/kg/day | tail nerve conduction velocity m/sec 4 wks after administration |
|---|---|---|
| Control group | 0 | 43.0 ± 0.5 |
| Diabetes grou | 0 | 38.8 ± 0.5 |
| Compound A-4 Administered group | 0.3 | 40.9 ± 0.5** |
| Compound A-4 Administered group | 1 | 41.3 ± 0.4** |
| Compound A-4 Administered group | 3 | 41.7 ± 0.5** |

The data was shown by mean±standard error of 10 rats per group. Each group administered with the compound was compared to diabetes group by Dunnett's test (**P<0.01).

From the above-mentioned results of Experimental Examples, the compound A-2 and compound A4 of the present invention suppressed decrease in tail nerve conduction velocity in a dose-dependent manner.

Experimental Example 2

A 0.5% hydroxypropylmethylcellulose suspension containing the compound of the present invention was orally administered to 9-week-old male spontaneously diabetic mice (db/db) once a day. At 4–5 weeks from the administration, sciatic nerve conduction velocity was measured with an induction potential test device (Neuropack 2, manufactured by Nihon Kohden) according to a modification of the method of Yasuda (Diabetes, 38, p. 832–838 (1989)). To be specific, rectal temperature was maintained at 37° C. and two points of sciatic notch and ankle were percutaneously stimulated electrically. The distance between the stimulation points was divided by the difference between latencies in induced electromyogram to give nerve conduction velocity.

TABLE 4

| test group | dose mg/kg/day | sciatic nerve conduction velocity m/sec 4 wks after administration |
| --- | --- | --- |
| Diabetes group | 0 | 44.3 ± 1.1 |
| Compound A-2 Administered group | 0.05 | 46.6 ± 1.5 |
| Compound A-2 Administered group | 0.5 | 51.9 ± 1.2** |
| Compound A-2 Administered group | 5 | 51.7 ± 1.4** |

The data was shown by mean±standard error of 7–9 mice per group. Each group was compared to diabetes group by Dunnett's test (**P<0.01).

TABLE 5

| test group | dose mg/kg/day | sciatic nerve conduction velocity m/sec 5 wks after administration |
| --- | --- | --- |
| Diabetes group | 0 | 39.6 ± 1.2 |
| Compound A-4 Administered group | 0.3 | 45.2 ± 1.2** |
| Compound A-4 Administered group | 1 | 45.9 ± 0.7** |
| Compound A-4 Administered group | 3 | 45.3 ± 0.8** |

The data was shown by mean±standard error of 8–9 mice per group. Each group was compared to diabetes group by Dunnett's test (**P<0.01).

From the above-mentioned results of Experimental Examples, the compound A-2 and compound A4 of the present invention increased sciatic nerve conduction velocity of spontaneous diabetic mice.

Experimental Example 3

Diabetes was induced by intravenous administration of steptozotocin (65 mg/kg) to 6week-old male Sprague-Dawley rats. Stating from 16 weeks after the onset of diabetes, a 0.5% hydroxypropylmethylcellulose suspension containing compound A-1 was orally administered once a day. At 5 weeks from the administration, tail nerve conduction velocity was measured with an induction potential test device (Neuropack 2, manufactured by Nihon Kohden) according to a modification of the method of Miyoshi (Fukuoka Medical Journal, vol. 62, pp. 588–603 (1971)). To be specific, subcutaneous temperature at the tail was maintained at 37° C. and the tail nerve was percutaneously stimulated electrically at 2 stimulation points (interval 6 cm). The distance between the stimulation points was divided by the difference between latencies in induced electromyogram to give nerve conduction velocity.

TABLE 6

| test group | dose mg/kg/day | tail nerve conduction velocity (m/sec) | |
| --- | --- | --- | --- |
| | | before administration | 5 wks after administration |
| Control group | 0 | 54.0 ± 0.5 | 54.4 ± 0.5 |
| Diabetes group | 0 | 46.4 ± 0.5 | 46.9 ± 0.3 |
| Compound A-1 Administered group | 0.3 | 46.2 ± 0.5 | 48.3 ± 0.6 |
| Compound A-1 Administered group | 1 | 46.1 ± 0.4 | 49.4 ± 0.4** |
| Compound A-1 Administered group | 3 | 46.0 ± 0.3 | 50.2 ± 0.5** |

The data was shown by mean±standard error of 10 rats per group. Each group administered with the compound was compared to diabetes group by Dunnett's test (P<0.01).

From the above-mentioned results of Experimental Example, the compound A-1 increased tail nerve conduction velocity that had been lowered by the progression of diabetes, in a dose-dependent manner.

Experimental Example 4

Diabetes was induced by intravenous administration of streptozotocin (65 mg/kg to 5-week-old male Sprague-Dawley rats. Starting from 9 weeks after the onset of diabetes, a 0.5% hydroxypropylmethylcellulose suspension containing compound A-1 was orally administered once a day. At 9 weeks from the administration, kidney was removed to determine the degree of glomerular disorder and fixed in a 10% neutral-buffered formalin solution. Tissue sections were stained with hematoxylin/eosin. Glomerulus was evaluated according to the degree of obstruction in 5 stages (0: no obstruction, 1: up to 25% obstruction, 2: up to 50% obstruction, 3: up to 75% obstruction, 4: up to 100% obstruction). Fifty glomeruli were evaluated per sample and the total score was used as an index of the degree of glomerular disorder. This operation was done under a single blind condition.

TABLE 7

| test group | dose mg/kg/day | n | glomerular disorder score |
| --- | --- | --- | --- |
| Diabetes group | 0 | 9 | 90.2 ± 7.9 |
| Compound A-1 Administered group | 0.3 | 5 | 90.8 ± 10.0 |
| Compound A-1 Administered group | 1 | 7 | 65.7 ± 12.0 |
| Compound A-1 Administered group | 10 | 8 | 55.4 ± 9.2* |

The data was shown by mean±standard error. Each group was compared to diabetes group by Dunnett's test (*P<0.05).

From the above-mentioned its of Experimental Example, the compound A-1 of the present invention suppressed glomerular disorder due to diabetes in a dose-dependent manner.

Experimental Example 5

Diabetes is induced by intravenous administration of streptozotocin (65 mg/kg) to 6week-old male Sprague-Dawley rats. Starting from 2 weeks after the onset of diabetes, a 0.5% hydroxypropylmethylcellulose suspension containing compound A-1 is orally administered once a day. Urine is taken with the passage of time for 24 hours at several weeks' interval. The amount of urinary albumin excretion is determined by enzyme immunoassay. In addition, retina is photographed and examined by counting neogenetic blood vessels. After the completion of the drug administration, the rats are killed and blood vessels, such as aorta, are taken to make tissue samples. The sample stained with hematoxylin/eosin is observed with an optical microscope to quantitatively determine the degree of tunica intima.

From the above-mentioned Formulation Examples and Pharmacological Experiments, it is clear that the pharmaceutical agent of the present invention is useful for the prophylaxis and treatment of diabetic complications, namely, diabetic neuropathy, nephropathy, ophthalmopathy, arteriosclerosis and the like. The action of the drug is long-lasting for very small doses and a single administration a day is sufficient

What is claimed is:

1. A method for the prophylaxis and treatment of diabetic neuropathy, comprising administering an effective amount of 4-[$\alpha$-hydroxy-2-methyl-5-(1-imidazolyl)benzyl]-3,5-dimethylbenzoic acid, an optically active compound thereof or a pharmaceutically acceptable salt thereof.

2. A method for the prophylaxis and treatment of diabetic neuropathy, comprising admit an effective amount of sodium 4-[$\alpha$-hydroxy-2-methyl-5-(1-imidazolyl)benzyl]-3,5dimethylbenzoate dihydrate.

3. A method for the prophylaxis and treatment of diabetic neuropathy, comprising administering an effective amount of (S)-(-)-4-[$\alpha$-hydroxy-2-methyl-5-(1l-imidazolyl)benzyl]3,5-dimethylbenzoic acid or a pharmaceutically acceptable salt thereof.

4. A method for the prophylaxis and treatment of diabetic neuropathy, comprising administering an effective amount of sodium (S)-(-)-4-[$\alpha$-hydroxy-2-methyl-5-(1-imidazolyl)benzyl]-3,5-dimethylbenzoate 2/3 hydrate.

* * * * *

UNITED STATES PATENT AND TRADEMARK OFFICE
CERTIFICATE OF CORRECTION

PATENT NO. : 6,060,496
DATED : May 9, 2000
INVENTOR(S) : Yoshiharu HAYASHI et al.

It is certified that error appears in the above-identified patent and that said Letters Patent is hereby corrected as shown below:

On the abstract page, the assignee information should read:

--[73] Assignee: Yoshitomi Pharmaceutical Industries, Ltd., Japan--

Column 12, line 5, change "admit" to --administering--;
line 7, change "5dimethyl" to --5-dimethyl--;
line 10, change "11-imidazolyl" to --1-imidazolyl--;
line 12, change "]3,5-dimethyl" to --]-3,5-dimethyl--.

Signed and Sealed this

Twenty-fourth Day of April, 2001

Attest:

NICHOLAS P. GODICI

Attesting Officer

Acting Director of the United States Patent and Trademark Office